United States Patent
Hocking (10) Patent No.: US 6,615,653 B1
(45) Date of Patent: Sep. 9, 2003

(54) IN SITU METHOD FOR DETERMINING SOIL LIQUEFACTION TENDENCY AND ITS PREVENTION BY ELECTRO-OSMOSIS

(75) Inventor: Grant Hocking, Alpharetta, GA (US)

(73) Assignee: GeoSierra, LLC, Atlanta, GA (US)

( * ) Notice: Subject to any disclaimer, the term of this patent is extended or adjusted under 35 U.S.C. 154(b) by 0 days.

(21) Appl. No.: 09/965,317

(22) Filed: Sep. 27, 2001

(51) Int. Cl.[7] .................. F02D 3/08; G01N 15/08; G01N 3/42; G01N 3/00; G01V 7/00
(52) U.S. Cl. .................. 73/152.01; 73/152.06; 73/152.51; 73/38; 702/2; 405/36; 405/37; 324/347; 324/353
(58) Field of Search .................. 73/152.01, 152.06, 73/152.22, 152.38, 152.51, 37–38, 73; 702/2, 6; 405/80, 36, 37; 324/347, 353

(56) References Cited

U.S. PATENT DOCUMENTS

| | | | | |
|---|---|---|---|---|
| 3,457,778 A | * | 7/1969 | Gill et al. ................ | 73/84 |
| 4,554,819 A | * | 11/1985 | Ali et al. ................ | 73/9 |
| 4,594,899 A | * | 6/1986 | Henke et al. ............. | 73/784 |
| 4,884,436 A | * | 12/1989 | Ankeny et al. ........... | 73/38 |
| 4,956,993 A | * | 9/1990 | Mehler .................... | 73/38 |
| 4,960,524 A | * | 10/1990 | Inculet et al. ........... | 210/747 |
| 5,417,104 A | * | 5/1995 | Wong ...................... | 73/38 |
| 5,548,991 A | * | 8/1996 | Ritson .................... | 73/38 |
| 5,668,306 A | * | 9/1997 | Doherty ................... | 73/38 |
| 5,689,068 A | * | 11/1997 | Locatelli et al. ......... | 405/36 |
| 5,800,090 A | | 9/1998 | Goughnour ................ | 405/36 |
| 6,098,448 A | * | 8/2000 | Lowry et al. .............. | 73/38 |
| 6,208,940 B1 | * | 3/2001 | Kram et al. ............... | 702/12 |
| 6,308,135 B1 | * | 10/2001 | Hocking .................. | 702/2 |

OTHER PUBLICATIONS

International Search Report, dated Feb. 14, 2003, for International Application No. PCT/US02/30235, 6 pages.

* cited by examiner

Primary Examiner—Hezron Williams
Assistant Examiner—David J. Wiggins
(74) Attorney, Agent, or Firm—Smith, Gambrell & Russell, LLP (57) ABSTRACT

A method for determining the liquefaction tendency of a water saturated soil is provided in which a driven or self boring probe with a plurality of expanding and contracting bladders imposes a cyclic shear stress reversal on a body of soil in situ, and from the measurement of pore water pressure, the liquefaction potential of the soil can be quantified. A pore water pressure increase during cyclic shear stress reversals indicates a contractive soil which has the potential to liquefy. The method can also quantify the potential of electro-osmosis in preventing soil liquefaction, by energizing a group of at least three electrodes by a d-c power source during the potential onset of liquefaction, and measure the reduction in pore water pressure during subsequent repeated shear stress reversals imposed on the soil by the device.

25 Claims, 6 Drawing Sheets

IN SITU METHOD FOR DETERMINING SOIL LIQUEFACTION TENDENCY AND ITS PREVENTION BY ELECTRO-OSMOSIS

TECHNICAL FIELD

This invention relates to an in situ method for quantifying the liquefaction tendency of water saturated soils, and for determining the potential of electro-osmosis to prevent soil liquefaction.

BACKGROUND OF THE INVENTION

Soil liquefaction results from an increase in soil pore water pressure induced by transient or repeated ground motions or shocks. Pore water increases may be induced by earthquakes, explosions, impacts, and ocean waves. Soil liquefaction occurs in water saturated, cohesionless soils and causes a loss of soil strength that may result in the settlement and/or failure of buildings, dams, earthworks, embankments, slopes, and pipelines. Liquefaction of sands and silts has been reported in almost all of the major earthquakes around the world. The imposed ground stress waves from earthquakes or other transient or repeated loading induces shaking or vibratory shearing of saturated loose fine sand or silts, causing a phenomenon known as liquefaction. When loose sands and silts are subjected to repeated shear strain reversals, the volume of the soil contracts and results in an immediate rise in the pore water pressure within the soil. If the pore water pressure rises sufficiently high, then the soil grain to grain contact pressure drops to zero, and the soil mass will lose all shear strength and temporarily act like a fluid, i.e. an occurrence of liquefaction occurs. Such temporary loss of shear strength can have a catastrophic effect on earthworks or structures founded on these deposits. Major landslides, settling or tilting of buildings and bridges and instability of dams or tailings ponds and failure of pipelines have all been observed in recent years and efforts have been directed to prevent or reduce such damage.

The factors that effect the occurrence of liquefaction are soil type, grain size distribution, compactness of the soil, soil permeability, magnitude and number of the shear strain reversals. Fine sand or fine cohesionless soils containing moderate amounts of silt are most susceptible to liquefaction. Uniformly graded soils are more susceptible to liquefaction than well graded soils, and fine sands tend to liquefy more easily than coarse sands or gravelly soils. Moderate amounts of silt appear to increase the liquefaction susceptibility of fine sands; however, fine sands with large amounts of silt are less susceptible although liquefaction is still possible. Recent evidence indicates that sands containing moderate amounts of clay may also be liquefiable.

In very coarse sands or gravel, ground water can flow freely enough that pore water pressures never become dangerously high to give rise to liquefaction. Fine sands and silty sands however have moderate to low permeability, which prevents the dissipation of induced pore water pressures and results in liquefaction of the soil. If the soil pore water pressures generated during an earthquake event can be relieved, then the soil will not liquefy and hence will remain stable.

Conventional soil stabilization methods to minimize or prevent liquefaction consist of one of five general methods:

1) remove liquefaction prone soil material and replace with sound material,
2) provide structural support to underlying firm soil strata, e.g. piling,
3) densify the soil to render it less susceptible to liquefaction,
4) strengthen the liquefaction prone soils,
5) provide drainage to prevent build up of soil pore water pressures, e.g. stone or gravel columns or relief wells.

The above methods have proven successful in minimizing liquefaction related damage; however, they are expensive, difficult to implement in existing structures and some of the methods are severely limited in their effectiveness in fine grain soils. An alternative method of preventing soil liquefaction involves activating an electro-osmotic gradient away from the foundation of the structure or towards a series of pressure relief wells, and thus negate the impact of the earthquake shaking on raising the soil pore water pressure and hence maintain the soil shear strength and structural stability.

Electro-osmosis involves the application of a constant d-c current between electrodes inserted in the saturated soil, that gives rise to pore fluid movement from the source electrodes towards the sink electrodes and thus modifies the soil pore water pressures. Electro-osmosis has been used in applications such as 1) improving stability of excavations, 2) decreasing pile driving resistance, 3) increasing pile strength, 4) stabilization of soils by consolidation or grouting, 5) dewatering of sludges, 6) groundwater lowering and barrier systems, 7) increasing petroleum production, 8) removing contaminants from soils, and 9) for preventing liquefaction of soils during earthquake events. Electro-osmosis uses a d-c electrical potential difference applied across the saturated soil mass by electrodes placed in an open or closed flow arrangement. The d-c potential difference sets up a constant d-c current flowing between the source and sink electrodes. In most soils the soil particles have a negative charge. In those negatively charged soils, the source electrode is the anode electrode and the sink electrode is the cathode electrode, and ground water migrates from the anode electrode toward the cathode electrode. In other soils, such as calcareous soils, the soil particles carry a positive charge. In those positively charged soils, the source electrode is the cathode electrode, the sink electrode is the anode electrode, and ground water migrates from the cathode electode toward the anode electrode.

An "open" flow arrangement of the electrodes allows an ingress or egress of the pore fluid. Due to the electrically induced transport of pore water fluid, the soil pore water pressures are modified to enable excavations to be stabilized or pile driving resistance to be lowered. Electro-osmosis is not used extensively due to the high cost of maintaining the d-c potential over long periods of time and the drying out and chemical reactions that occur if the system is activated for long periods of time. For short term stabilization by pore water pressure reduction, electro-osmosis is very effective in fine grained soils, such as fine sands, silty sands, and silts.

For existing or planned structures, the liquefaction tendencies of a site need to be examined and quantified so that preventive measures can be incorporated into the design of the planned structure or the existing structure be appropriately modified. Therefore, there is a need for a definitive method of measuring the liquefaction potential of a soil in situ, quantifying under what loading conditions the soil will liquefy, and also in determining if liquefaction preventative measures such as electro-osmosis are applicable.

Prior methods for evaluating the liquefaction potential of soils consist of two basic approaches, laboratory tests and in situ tests. The laboratory methods require undisturbed soil samples which are difficult to impossible to obtain. The laboratory test methods involve cyclic triaxial, cyclic direct shear, and cyclic torsional triaxial tests. All of these tests apply a cyclic shear stress reversal upon the soil specimen. At the present time, there is not a method for obtaining undisturbed samples, in which the in situ stress state, void ratio, or structure have been preserved in cohesionless soils. Therefore, laboratory methods are considered only qualitative tests in assessing the potential of a soil to liquefy. The in situ methods currently consist of five (5) types, with four (4) of the methods being indirect empirical methods and the fifth ($5^{th}$) method being a direct in situ measurement of a soil's shear strength and an inferred method for quantifying a soil's potential to liquefy. The four (4) indirect empirical methods are; 1) the Standard Penetration Test (SPT); 2) the Cone Penetration Test (CPT); 3) the Piezocone Penetration Test (PCPT) and 4) the Seismic Waves Test (SWT). The fifth direct in situ measurement is the Piezo Vane Test (PVT).

The Standard Penetration Test (SPT) approach is based on an empirical correlation between the number of blows of a probe to penetrate the soil correlated to the observed occurrence or non-occurrence of liquefaction of particular soils during past earthquake events. The Cone Penetration Test (CPT) has several advantages over the SPT, but like the SPT test, involves correlating cone penetration resistance to the observed occurrence or non-occurrence of liquefaction of sites during past earthquake events. The Piezocone Penetration Test (PCPT) is similar to the CPT test except that pore water pressure measurements are recorded during driving of the cone into the soils, however the quantification of a soil's potential to liquefy is based on similar empirical relationships as the CPT test, resulting in this test having the same basic disadvantages and deficiencies as the CPT method. The Seismic Waves Test (SWT) is based on empirical relationships between the seismic wave velocities of the soil as measured in situ to the observed occurrence or non-occurrence of liquefaction at sites during past earthquake events.

The Piezo Vane Test (PVT) involves the in situ failure of the soil under a shearing action by rotating a vane inserted into a borehole drilled into the soil. The method has been utilized primarily for quantifying the shear strength of cohesive soils; however, recently it has been applied to infer the potential of a soil to liquefy, by the measurement of pore water pressures during the shearing process. The method is based on shearing the soil under totally different stress states to that experienced during an earthquake, and in most cases the soils fail immediately. Therefore, the PVT does not impose shear stress reversals upon the soil that would be experienced during an actual earthquake event.

In situ pressure meter tests have been utilized for many years both for quantification of a soil's deformational properties but also its strength properties. These devices have either been inserted into a drill hole, driven or been self boring. Self boring pressure meters minimize any disturbance to the soil and thus only minimally deform the soil prior to the test. In the case of driven probes, empirical correction factors have been applied to account for the disturbance of the soil caused during driving of the device. Pressure meter devices have not been developed that can determine the potential of a soil to liquefy.

Therefore, there is an apparent need for a method of quantifying in situ a soil's potential to liquefy under transient and repeated loading such as experienced during an earthquake. Such a method has to cyclically place the soil in situ under stress conditions that are analogous to those generated during an earthquake, i.e. shear stress reversal. Also there is a need for a method to quantify in situ the impact of electro-osmosis in preventing soil liquefaction by reducing pore water pressures during cyclic shear stress reversals.

SUMMARY OF THE INVENTION

A method for determining the liquefaction potential of a water saturated soil is provided in which a driven or self boring probe with a plurality of expanding and contracting bladders imposes a cyclic shear stress reversal on a body of soil in situ, and the liquefaction potential of the soil can be quantified from the subsequent measurement of pore water pressure response during the cyclic shear stress reversals. A pore water pressure increase during cyclic shear stress reversals, indicates a contractive soil which has the potential to liquefy. The method can also quantify the potential of electro-osmosis in preventing soil liquefaction, by energizing electrodes by a d-c power source during the onset of liquefaction, and by measuring the reduction in pore water pressure during subsequent repeated shear stress reversals imposed on the soil by the device.

The present invention is a method for determining in situ the liquefaction potential of a water saturated soil by placing a body of soil under cyclic shear stress reversals, under zero volume change, and undrained pore water conditions and by measuring the subsequent induced pore water pressure response. A pore water pressure increase during cyclic shear stress reversals indicates a contractive soil which has the potential to liquefy. The cyclic shear stress reversal is imposed on the soil by a driven or self boring probe with a plurality of expanding and contracting bladders which impose a cyclic stress reversal on a body of soil in situ. The simultaneous expansion and contraction of the bladders under a zero volume change condition is achieved by cyclic upward and downward vertical movement of a piston inside a fluid pressure cylinder connected to the plurality of bladders. The fluid system ensures the bladders are simultaneously expanded and contracted under zero volume change. The soil stress state varies from a horizontal maximum principal stress during the expansion phase of the bladder, and changes to a vertical maximum principal stress state during the contraction phase of the bladder. Thus the soil immediately in the zone of influence of the bladders undergoes shear stress reversals, much like that imposed in a cyclic triaxial laboratory test, except that the test is conducted in situ on an undisturbed soil mass. The pore water pressure in the soil is measured during this cyclic shear stress reversal loading which has been imposed under zero volume change and undrained conditions. The magnitude of the loading, number of cyclic shear stress reversals and change in pore water pressure quantifies the potential of the soil to liquefy.

The device is either driven to depth, much like a CPT, or inserted into a drilled borehole, or self bored into the soil. A self boring device imposes the minimal disturbance on the soil and thus provides direct measurement of a soil's potential for liquefaction. A driven device will slightly disturbed the soil during driving and generally strengthens and stiffens the soil from its undisturbed state. An empirical correlation relationship will need to be quantified to interpret the results from the driven probe to account for the slight modification of the soil's state from its original undisturbed in situ state. During insertion of the device to the correct depth horizon, the piston in the fluid pressure cylinder is held in the neutral or equilibrium position. Once at the measurement horizon, the device is clamped at the surface to prevent movement of the device by securing the outer most connecting rods. The data acquisition is activated, the bladders are cyclically expanded and contracted, and the pore water pressure response monitored to quantify the soil's potential to liquefy.

The piston driving the expansion and contraction of the bladders can be cyclically moved upwards and downwards either from the surface or by electro-mechanical or hydraulic means by suitable apparatus included down hole within the device. The frequency of the expansion and contraction of the bladders is conducted at similar frequencies to shear stress reversals experienced by soil during actual earthquake events, i.e. approximately 1 Hz. The pore water pressure can be measured by a number of devices, either similar to those in PCPT equipment, or by more precise devices such as a differential pressure gauge. The pore water pressure gauge can be a strain gauge device, a piezo-electric, a vibrating wire, or other device that provides an analogue output for connection and recording to a computerized data acquisition system. In addition to monitoring the pore water pressure, the data acquisition system also simultaneously records the piston motion via an instrumented Linear Variable Differential Transformer (LVDT) and the fluid pressure in each bladder by fluid pressure gauges. Thus the loading state, the frequency of loading, and the pore water pressure response can all be recorded by the computerized data acquisition system simultaneously. From analysis of these data, the potential of the soil to undergo liquefaction can be quantified.

Thus the liquefaction potential of the soil can be quantified in situ by the method and apparatus from the subsequent measurement of pore water pressure during the cyclic shear stress reversals imposed on the soil by the device under zero volume change and under undrained pore water conditions. A pore water pressure increase during cyclic shear stress reversals, indicates a contractive soil which has the potential to liquefy. The method and apparatus can also include the activation of a d-c potential difference across electrodes contained within the device to impose an electro-osmosis gradient from the soil mass, undergoing cyclic shear stress reversals, towards pore water pressure relief electrodes. The pressure relief or sink electrodes contained within the device are energized under a opposite polarity to the source or driving electrode, and the pressure relief or sink electrodes contain a pore water pressure relief inlet to allow pore water to enter the device under static or reduced hydraulic head conditions. The subsequent reduction in pore water pressure during the cyclic stress reversals by the electro-osmosis gradient is recorded electronically by the computerized data acquisition system, including the earlier recorded parameters plus the imposed d-c voltage and induced d-c current flowing through the soil across the electrodes. The pore water pressure relief inlets contained within the device can be opened by a variety of means either electro-mechanical, hydraulic, or mechanical means upon energizing the electrodes by the d-c power source. The potential of electro-osmosis to prevent liquefaction of the particular soil horizon can thus be quantified.

DETAILED DESCRIPTION

Figure 1:
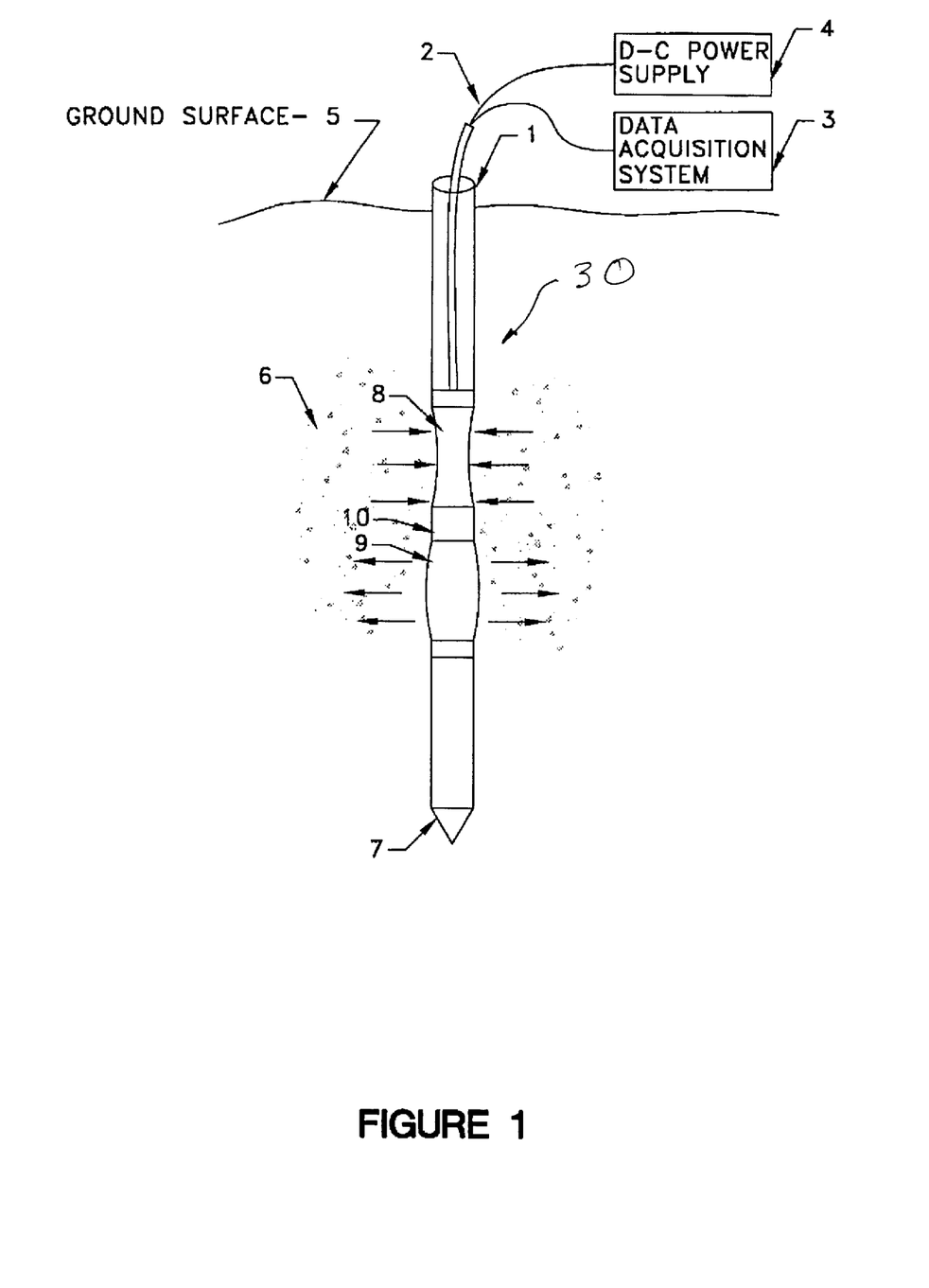
FIG. 1 is a cross sectional view showing one form of the invention for in situ inducing a cyclic shear stress reversal on the soil and measurement of the subsequent change in pore water pressure.

The present invention is a method and apparatus for determining in situ the liquefaction tendency of a water saturated soil by placing a body of soil under cyclic shear stress reversals, under zero volume change, and undrained pore water conditions and for measuring the subsequent induced pore water pressure response. One form of the invention is illustrated in cross section in FIG. 1, with a device 30 comprising multiple threaded outer rods 1 inside of which are electronic and power cables 2 from the device's sensors connected to both a computerized data acquisition system 3 and a d-c power supply 4. The device 30 is either driven or self bored from the surface 5 into a water saturated soil 6 to a particular depth for measurement of the soil's tendancy to liquefy. The driven device 30 contains a conventional instrumented PCPT cone tip 7 at its leading point, while a self boring device 30 contains a self boring element on its leading point similar to that available in conventional self boring soil pressure meter devices. The device 30 further consists of expanding and contracting bladders 8 and 9 which are cyclically alternated from expansion to contraction to load the soil under a zero volume change condition. The bladders 8 and 9 are constructed in a fashion that is similar to conventional fixed end packers. The bladders 8 and 9 are mounted on a central anvil, and each bladder contains an expanding and contracting reinforced rubber element. The pore water pressure within the soil undergoing the cyclic loading is measured by a pore water pressure gauge 10 contained within the device 30. The data acquisition system simultaneously records the expansion and contraction of the bladders 8 and 9 and the induced pore water pressure response from the gauge 10. The data can then be analyzed in the same manner used in connection with conventional laboratory tests.

Figure 2:
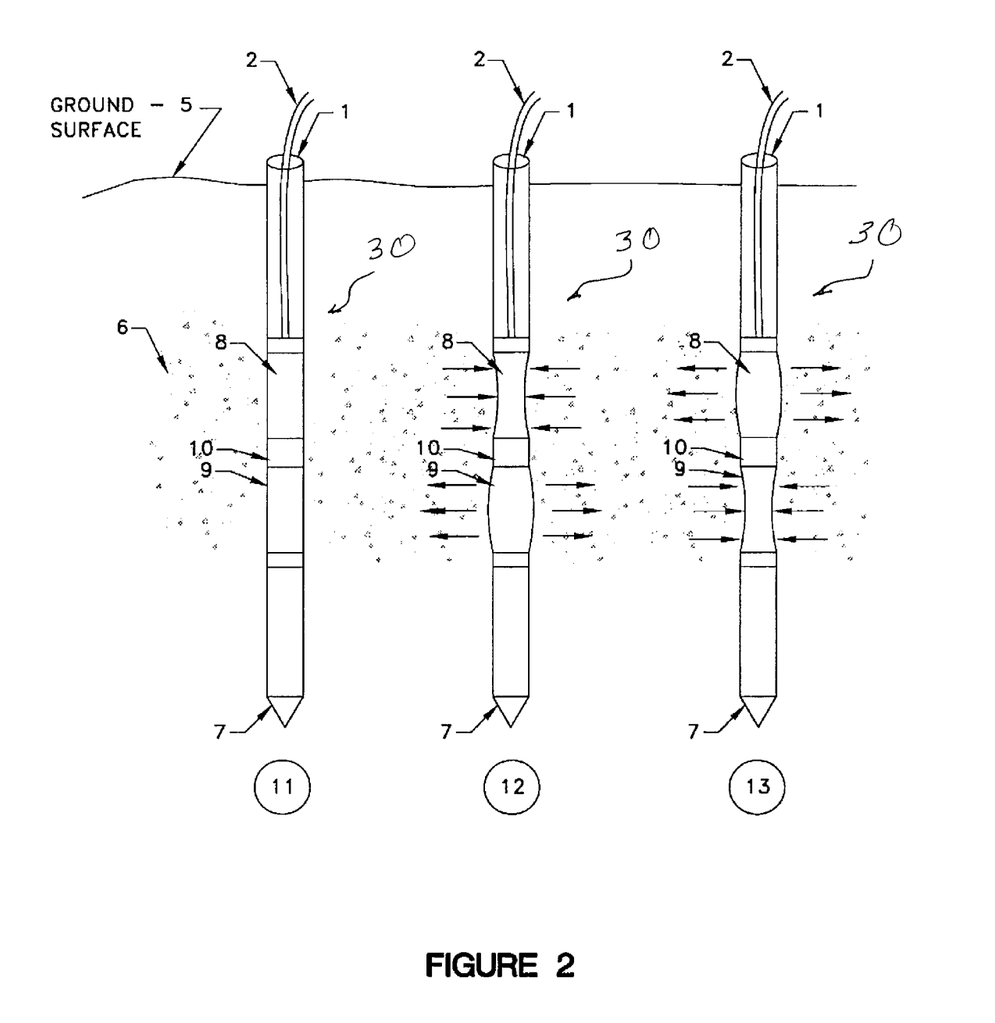
FIG. 2 is a cross sectional view showing one form of the invention in the equilibrium state and the two extreme expansion and contraction states.

The cyclic loading of the soil by the device 30 is shown further in FIG. 2, illustrating three states, the neutral or equilibrium state 11, the state 12 in which the bladder 8 is fully contracted and the bladder 9 is fully expanded, and the state 13 in which the bladder 9 is fully contracted and the bladder 8 is fully expanded. In the neutral or equilibrium state 11, the bladders 8 and 9 are in pressure equilibrium, and the bladders 8 and 9 are of the same size and volume. During the cyclic expansion and contraction of the bladders. 8 and 9, initially both bladders 8 and 9 are in the neutral or equilibrium state 11, then the uppermost bladder 8 is contracted by a volume change equal to the expansion of the lowermost bladder 9, to achieve the state 12. Following the state 12 of the bladders, the uppermost bladder 8 is then expanded through the equilibrium position 11 to its full expanded state 13, and simultaneously the lowermost bladder 9 is contracted through the equilibrium state 11 and then further contracted to its full contracted state 13. In state 12, the maximum principal stress state of the soil 6 is vertical immediately adjacent to the fully contracted bladder 8, and the maximum principal stress state of the soil 6 is horizontal immediately adjacent to the fully expanded bladder 9. Similarly in state 13, the maximum principal stress state of the soil 6 is horizontal immediately adjacent to the fully expanded bladder 8, and the maximum principal stress state of the soil 6 is vertical immediately adjacent to the fully contracted bladder 9. Thus the soil 6 undergoes shear stress reversals in the zones immediately adjacent to the bladders 8 and 9. The induced pore water pressure response is monitored by the pressure gauge 10 throughout the cyclic loading of the soil 6. The expansion and contraction of the bladders 8 and 9 is cyclically pulsed to the desired number of loading reversals as would be experienced as the result of a wave induced by an earthquake, a blast, or other transient repeated loading. For an earthquake event, the expansion and contraction of the bladders 8 and 9 should be at a frequency of approximately 1 Hz. For a blast, the expansion and contraction of the bladders 8 and 9 could be at a frequency as high as 10 Hz. Other transient loading may have frequencies as low as 0.01 Hz.

Figure 3:
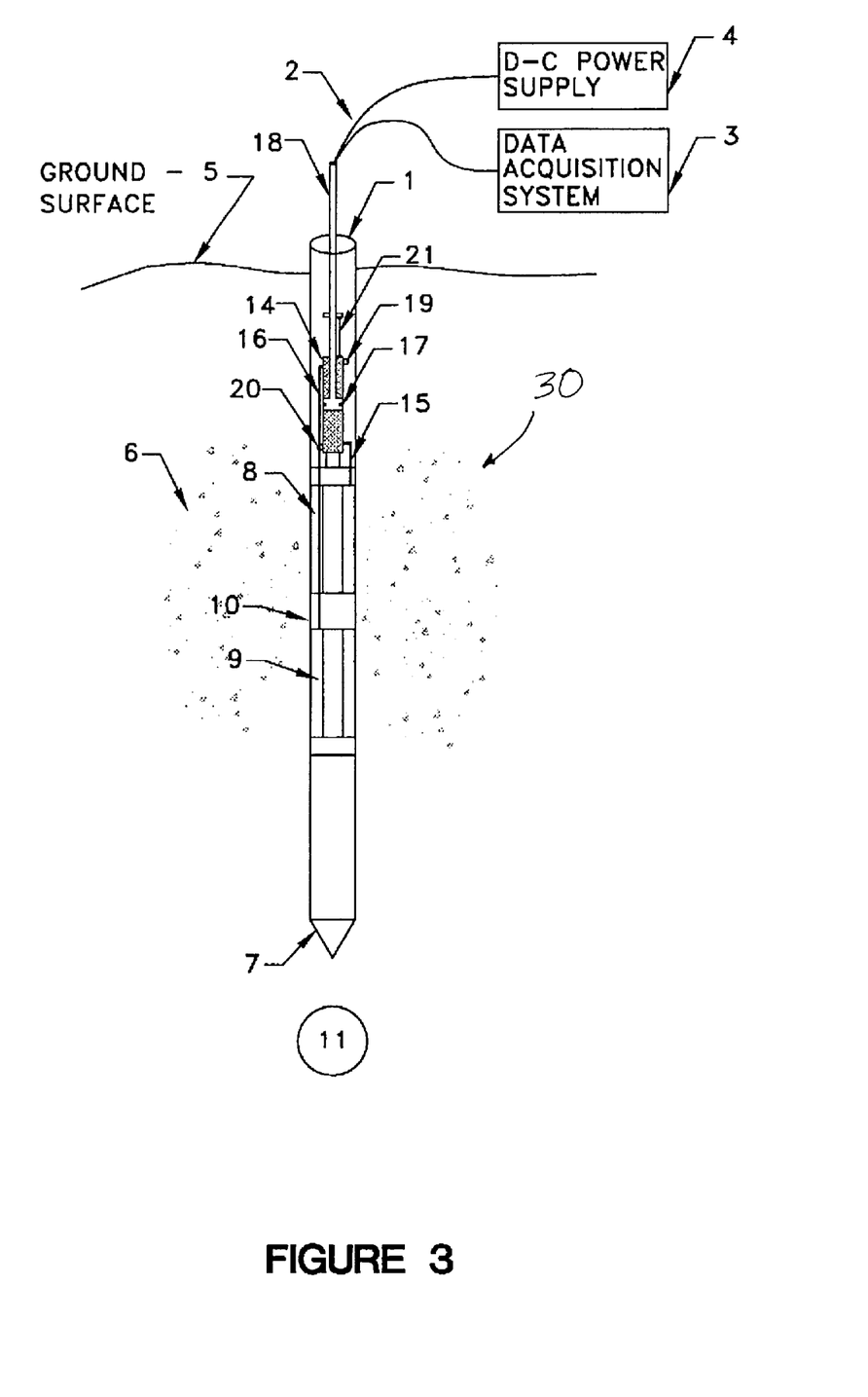
FIG. 3 is a cross sectional view showing one form of the invention involving a piston rod displacement to achieve the simultaneous expansion and contraction of the bladders shown in the neutral or equilibrium state.

One form of the invention to achieve the simultaneous expansion and contraction of the bladders 8 and 9 is shown in FIG. 3 in the neutral or equilibrium state 11. The expansion and contraction of the bladders 8 and 9 are driven by fluid contained in a pressure cylinder 14, connected by tubing 15 to the uppermost bladder 8 and also via tubing 16 to the lowermost bladder 9. The fluid is alternatively extracted from and injected into the bladders 8 and 9 by the vertical movement of a piston 17 connected to a driving rod 18. The pressure in each of the bladders 8 and 9 is monitored by pressure gauges 19 and 20 respectively and recorded on the data acquisition system 3. The vertical movement of the piston 17 is monitored by a linear variable differential transformer 21 or similar device, and the piston position is recorded on the data if acquisition system 3.

Figure 4:
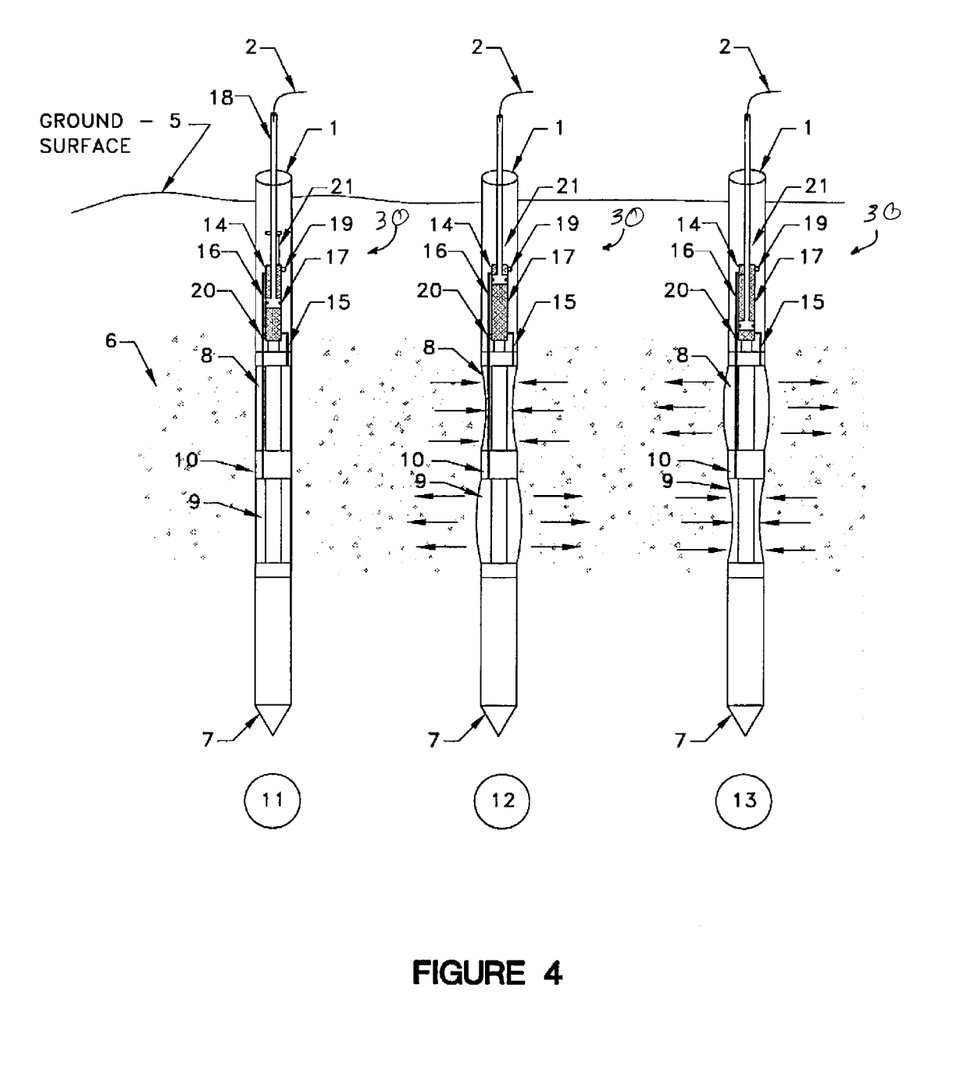
FIG. 4 is a cross sectional view showing one form of the invention involving a piston rod displacement to achieve the simultaneous expansion and contraction of the bladders shown in the neutral or equilibrium state and extreme expansion and contraction states for inducing a cyclic shear stress reversal on the soil in situ.

The three states of the cyclic expansion and contraction of the bladder 8 and 9 is shown on FIG. 4, the neutral or equilibrium state 11, the contraction/expansion state 12, and the expansion/contraction state 13. When the device 30 is in the neutral or equilibrium state 11, piston 17 is more or less centered within the fluid cylinder 14. Upward movement of the rod 18 moves the piston 17 in the fluid cylinder 14 to its uppermost position (state 12). In doing so, fluid is extracted from bladder 8 and injected into bladder 9 in a simultaneous controlled manner imposing no volume change on the soil 6. Downward movement of the rod 18 drives the piston 17 from the contraction/expansion state 12, through the neutral or equilibrium state 11, to the expansion/contraction state 13. At the expansion/contraction state 13, the piston 17 is at its lowermost position in the fluid cylinder 14. By movement of the piston 17 from the contraction/expansion state 12 to the expansion/contraction state 13, fluid is extracted from bladder 9 and injected into bladder 8. The fluid displacement by the piston 17 from the neutral or equilibrium state 11 to the contraction/expansion state 12 is controlled by movement of the rod 18 to be exactly the same as that displaced by the piston 17 from the neutral or equilibrium state 11 to the expansion/contraction state 13.

The cyclic movement of the rod 18 can be driven at the surface by a conventional hydraulic servo-controlled system or alternatively by electromechanical means using a solenoid or purely mechanical means. In another form of the invention the cyclic movement of the rod 18 could be activated and controlled down hole by either a hydraulic or electromechanical device contained within the device and controlled by instrumentation and power source from the surface. In either form of the invention the stroke of the piston 17 is controlled to achieve the desired expansion and contraction of the bladders 8 and 9 and thus loading on the soil. In addition, the frequency of the stroking of the piston 17 is controlled to achieve the desired loading rate on the soil.

Thus the loading state, the frequency of loading, and the pore water pressure response are all simultaneously recorded by the computerized data acquisition system. From analysis of these data, the tendency of the soil to undergo liquefaction can be quantified. The data from the in situ testing is analyzed in accordance with the methods used to analyze the data acquired in the standard laboratory tests for liquefaction.

Figure 5:
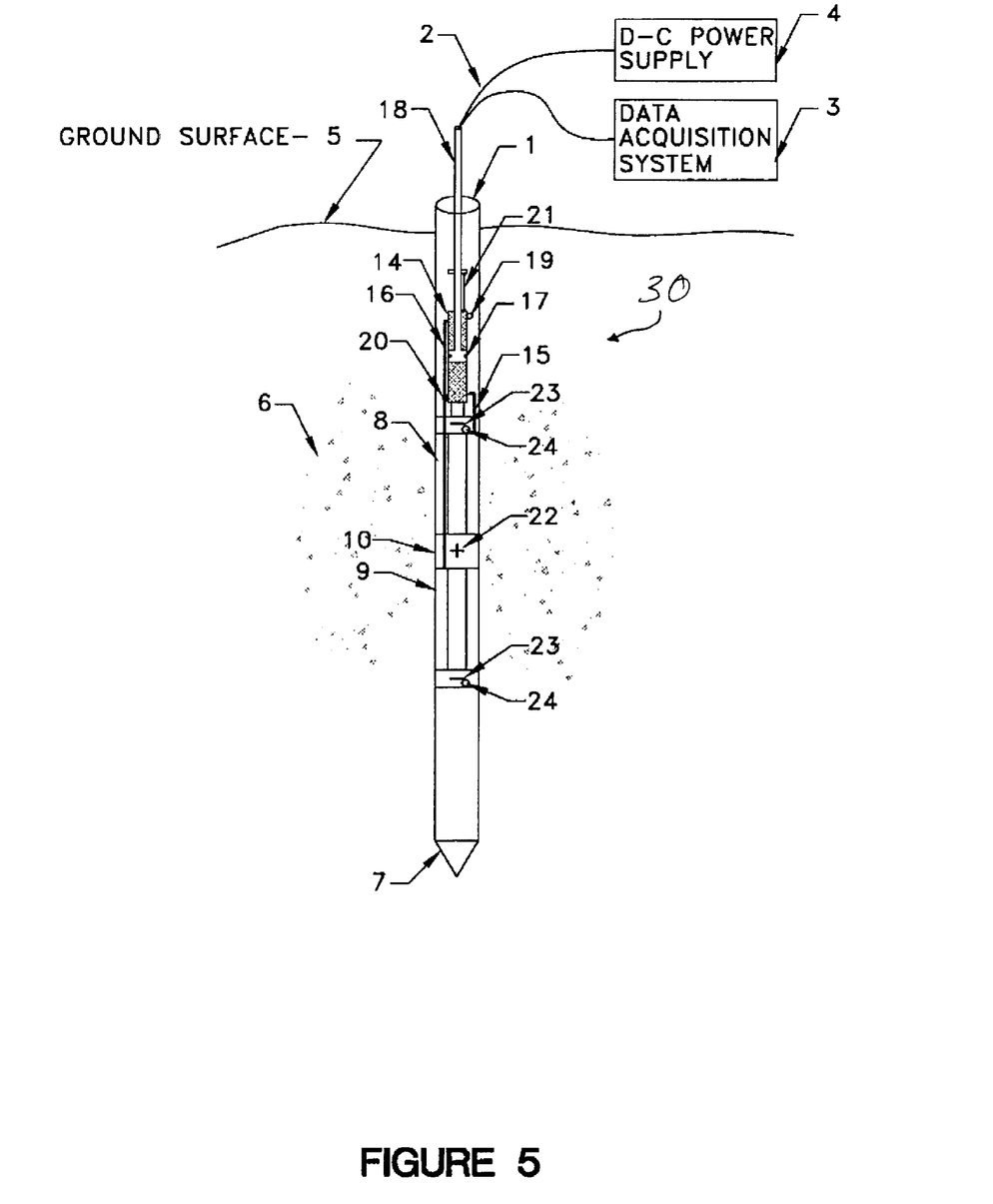
FIG. 5 is a cross sectional view showing one form of the invention for in situ inducing a cyclic shear stress reversal on the soil, concurrently energizing a set of electro-osmosis electrodes, opening pore water pressure relief ports in the device, and subsequently measuring of the change in pore water pressure.

In a modified form of the invention shown on FIG. 5 in the neutral or equilibrium state 11, the device contains a source or driving electrode 22, and two pressure relief or sink electrodes 23 with pore water pressure relief ports 24. The driving electrode is connected to one polarity of the d-c power supply 4 in this case denoted as positive. Therefore electrode 22 is an anode electrode. The pressure relief electrodes 23 are connected to the opposite polarity of the d-c power supply 4 and in this case denoted as negative. Therefore electrodes 23 are cathode electrodes. All of the electrodes 22 and 23 are electrically isolated and insulated from other parts of the device, and these electrodes are only electrically connected to the d-c power supply 4 and the water saturated soil 6.

Figure 6:
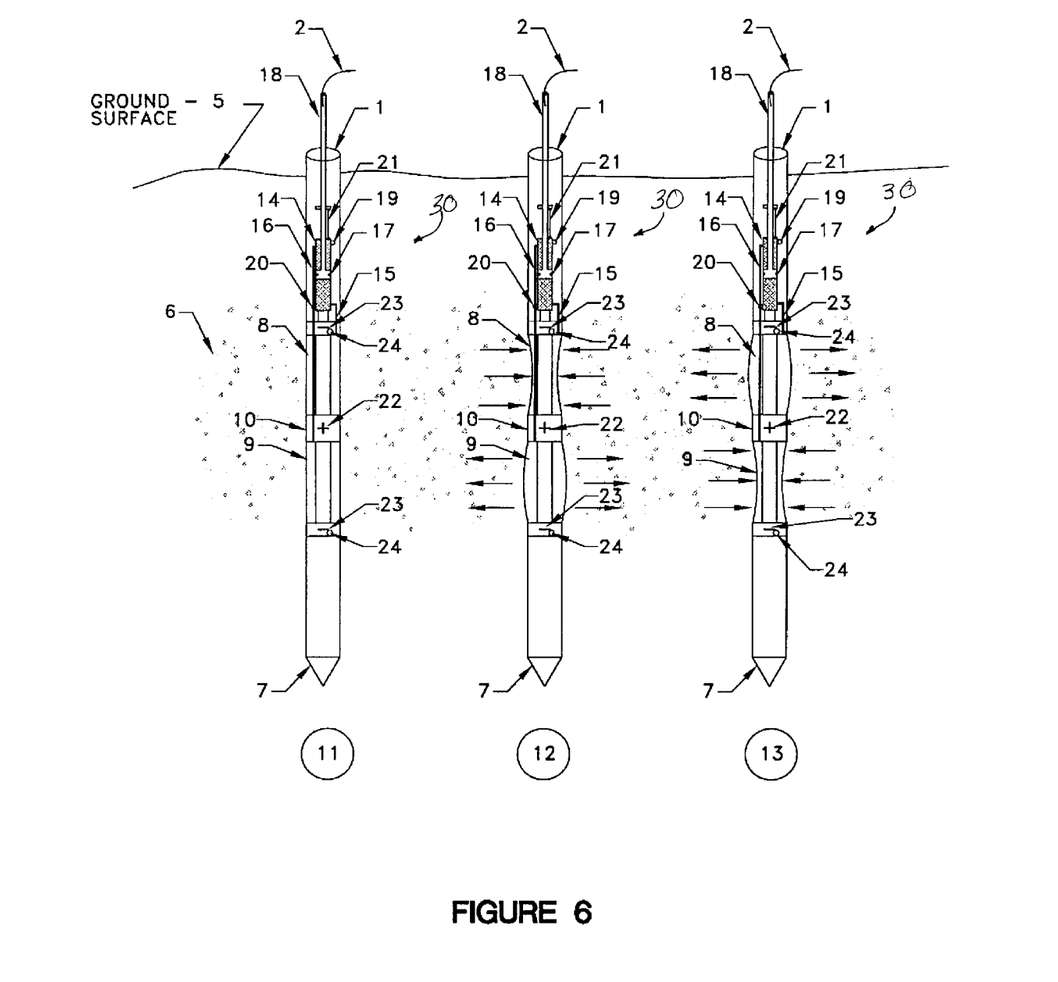
FIG. 6 is a cross sectional view showing one form of the invention in the equilibrium and extreme expansion and contraction states for in situ inducing a cyclic shear stress reversal on the soil, concurrently energizing a set of electro-osmosis electrodes, opening pore water pressure relief ports in the device, and subsequently measuring of the change in pore water pressure.

The three states of the cyclic expansion and contraction of the bladders are shown on FIG. 6, the neutral or equilibrium state 11, the contraction/expansion state 12, and the expansion/contraction state 13. During testing of a soil's tendency to liquefy, the device 30 imposes cyclic shear stress reversals on the soil 6 by the expansion and contraction of the bladders 8 and 9. If a rise in pore water pressure is detected by the pore water pressure gauge 10, then the device 30 with its electrodes 22 and 23 can quantify the potential of electro-osmosis in negating further pore water pressure in the soil 6 and thus its ability to prevent liquefaction of the soil. Upon detection of a rise in pore water pressure by the gauge 10 after a number of cyclic shear stress reversal loading on the soil 6, the electrodes 22 and 23 are energized by connection to the d-c power supply, and pressure relief ports 24 are opened within the device to allow pore water to be diverted into the device 30 under either static or reduced hydraulic head. The pore water pressure relief ports 24 can be opened by a variety of means, either electromechanical, hydraulically, or mechanical means. The pore water pressure relief ports 24 contain a porous element to stop soil from entering the relief port.

Thus the loading state, the frequency of loading, the pore water pressure response, the d-c applied voltage, and induced current are all simultaneously recorded by the computerized data acquisition system. From analysis of these data, the potential of electro-osmosis to prevent liquefaction of that particular soil horizon can be quantified.

The present invention, therefore, is well adapted to carry out the objects and attain the ends and advantages mentioned as well as others inherent herein. While presently preferred embodiments of the invention are given for the purpose of disclosure, numerous changes in the details of construction, arrangement of parts, and the steps of the process will readily suggest themselves to those skilled in the art and which are encompassed within the spirit of the invention and the scope of the appended claims.

What is claimed is:

1. An apparatus for determining liquefaction tendency of a soil in situ at a measurement depth horizon comprising:
   a plurality of expanding and contracting bladders in contact with the soil for cyclically loading the soil under a zero volume change condition;
   a pore water pressure sensor in contact with the soil for measuring the pore water pressure of the soil adjacent the bladders; and
   a data acquisition system for receiving the pore water pressure measurements from the soil during the cyclic loading.

2. The apparatus of claim 1, wherein the apparatus is self boring down to the measurement depth horizon.

3. The apparatus of claim 1, wherein the apparatus is driven down to the measurement depth horizon.

4. The apparatus of claim 1, wherein the apparatus is inserted into a pre-drilled borehole down to the measurement depth horizon.

5. The apparatus of claim 1, wherein the apparatus further comprises a piston in a fluid cylinder connected to the plurality of bladders, and movement of the piston extracts fluid from at least one deflating bladder and injects fluid into at least one inflating bladder to ensure the soil is cyclically loaded under a zero volume change condition.

6. The apparatus of claim 1, wherein the apparatus further includes sensors connected to the bladders for measuring a rate of change of expansion and contraction of the bladders and a fluid pressures inside of the bladders.

7. The apparatus of claim 1, wherein the apparatus consists of at least two expansion and contraction bladders.

8. An apparatus for determining if electro-osmosis can prevent an occurrence of liquefaction of a soil in situ at a measurement depth horizon comprising:
   a plurality of expanding and contracting bladders in contact with the soil for cyclically loading the soil at the measurement depth horizon under a zero volume change condition;
   a pore water pressure sensor in contact with the soil for measuring the pore water pressure of the soil adjacent the bladders;
   a d-c power source;
   an array of electrodes connected to the d-c power source positioned in the apparatus and in contact with the soil, wherein a d-c current flows through the electrodes as result of an applied d-c voltage from the d-c power source;
   a pore water pressure relief port located in the apparatus and adjacent to at least one of the conductors; and
   a data acquisition system for receiving the pore water pressure measurements from the soils during the cyclic loading.

9. The apparatus of claim 8, wherein the apparatus is self boring down to the measurement depth horizon.

10. The apparatus of claim 8, wherein the apparatus is driven down to the measurement depth horizon.

11. The apparatus of claim 8, wherein the apparatus is inserted into a pre-drilled borehole down to the measurement depth horizon.

12. The apparatus of claim 8, wherein the apparatus further comprises a piston in a fluid cylinder connected to the plurality of bladders, and movement of the piston extracts fluid from at least one deflating bladder and injects fluid into at least one inflating bladder to ensure the soil is cyclically loaded under zero volume change condition.

13. The apparatus of claim 8, wherein the apparatus further includes sensors connected to the bladders for measuring a rate of change of expansion and contraction of the bladders, fluid pressures inside of the bladders, the applied d-c voltage to the electrodes, and the induced d-c current between the electrodes.

14. The apparatus of claim 8, apparatus the device consists of at least two expansion/contraction bladders.

15. The apparatus of claim 8, wherein the apparatus consists of at least two electrical electrodes.

16. The apparatus of claim 8, wherein the apparatus consists of at least one pore water pressure relief ports.

17. An method for determining liquefaction tendency of a soil in situ at a measurement depth horizon comprising:
   cyclically loading the soil under a zero volume change condition;
   measuring the pore water pressure of the soil during the cyclic loading; and
   recording the pore water pressure measurements of the soils during the cyclic loading.

18. The method of claim 17, wherein the method further includes cyclically loading the soil at a predetermined frequency and recording the frequency.

19. The method of claim 17, wherein the method further includes measuring a rate of change in the cyclic loading of the soil and recording the rate of change.

20. The method of claim 17, wherein the cyclic loading of the soil is imposed on the soil in two adjacent regions.

21. A method for determining if electro-osmosis can prevent liquefaction of a soil in situ at a measurement depth horizon comprising:
   cyclically loading the soil under a zero volume change condition;
   measuring the pore water pressure of the soil during the cyclic loading;
   applying a d-c voltage to the soil to induce a d-c current in the soil;
   providing pore water pressure relief within the soil subject to the cyclic loading; and
   recording the pore water pressure measurements of the soils during the cyclic loading.

22. The method of claim 21, wherein the method further includes cyclically loading the soil at a predetermined frequency and recording the frequency.

23. The method of claim 21, wherein the method further includes measuring a rate of change in the cyclic loading of the soil and recording the rate of change.

24. The method of claim 21, wherein the method further includes measuring the applied d-c voltage, the induced d-c current in the soil, and recording the applied d-c voltage and the induced d-c current.

25. The method of claim 21, wherein the cyclic loading of the soil is imposed on the soil in two adjacent regions.

* * * * *